United States Patent
Cremer et al.

(12)

(10) Patent No.: US 6,569,621 B1
(45) Date of Patent: May 27, 2003

(54) METHOD OF PURIFYING DNA

(76) Inventors: Thomas Cremer, Institut für Anthropologie und Humangenetik, Richard Wagner Strasse 10/1, D-80333 Müchen (DE); Jeffrey Craig, The Murdoch Institute, Royal Children's Hospital, Flemington Road, Parkville 3052, Melbourne (AU)

( * ) Notice: Subject to any disclaimer, the term of this patent is extended or adjusted under 35 U.S.C. 154(b) by 0 days.

(21) Appl. No.: 09/269,715
(22) PCT Filed: Aug. 1, 1997
(86) PCT No.: PCT/EP97/04199
§ 371 (c)(1),
(2), (4) Date: Aug. 2, 1999
(87) PCT Pub. No.: WO98/15649
PCT Pub. Date: Apr. 16, 1998

(30) Foreign Application Priority Data

Oct. 4, 1996 (EP) .............................. 96115977

(51) Int. Cl.[7] .......................... C12Q 1/68; C12P 19/34; C12M 1/34; C07H 21/02
(52) U.S. Cl. .......................... 435/6; 435/91.2; 435/270; 435/287.2; 436/94; 536/23.1; 536/24.33

(58) Field of Search .................. 435/6, 91.1, 91.2, 435/183, 287.1, 287.2, 270; 436/94, 501; 530/350, 387.1; 536/23.1, 24.33

(56) References Cited

U.S. PATENT DOCUMENTS

| 5,200,313 A | * | 4/1993 | Carrico | 435/6 |
| 5,589,339 A | * | 12/1996 | Hampson et al. | 435/6 |
| 5,882,874 A | * | 3/1999 | Fisher | 435/6 |

OTHER PUBLICATIONS

Chen–Liu et al., Genomics, vol. 30, 195, pp. 388–392.*
Rouquier et al. Nucleic Acids Research, 1995, vol. 23, No. 21, pp. 4415–4420.*

* cited by examiner

Primary Examiner—Bradley L. Sisson
(74) Attorney, Agent, or Firm—Piper Rudnick LLP; Steven B. Kelber

(57) ABSTRACT

The present invention relates to a method of purifying a set of specific DNA molecules to be used in DNA-DNA hybridisations, as well as to DNA probes containing less than 2% Cot-1 DNA.

29 Claims, 3 Drawing Sheets

METHOD OF PURIFYING DNA

Figure 1A:
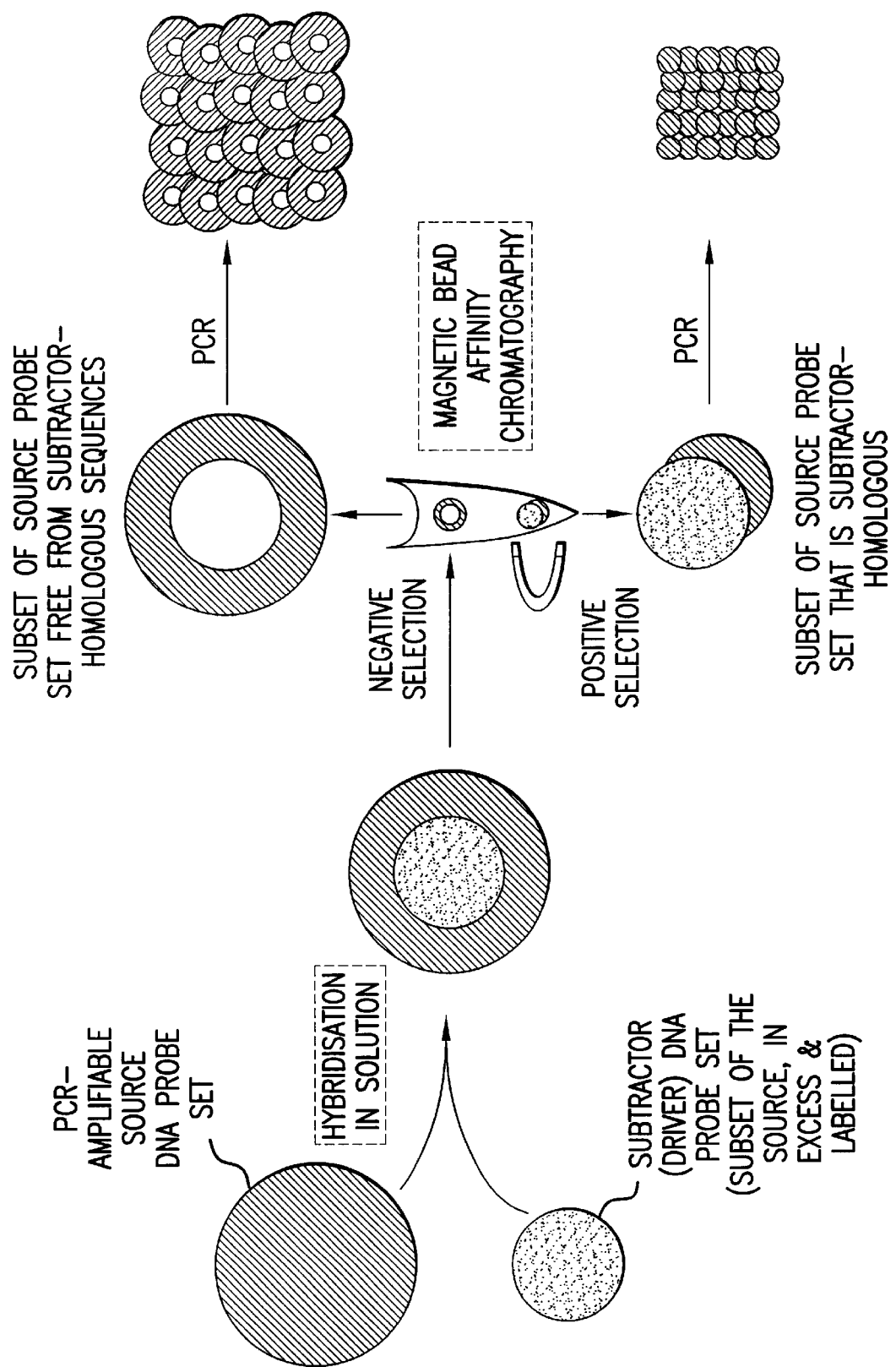

The present invention relates to a method of purifying a set of specific DNA molecules to be used in DNA-DNA hybridisations, as well as to DNA probes containing less than 2% Cot-1 DNA.

Molecular genetics is the study of nucleic acids and their role in the biology of the cell. At the core of this science is the technique of Southern blotting, which involves the hybridisation of DNA in solution to DNA immobilised on a solid membrane. One relatively new branch of molecular genetics, molecular cytogenetics, deals with the molecular biology of the chromosome level of organisation as opposed to the DNA level. The field of molecular cytogenetics is a steadily expanding field whose broad implications for the study of human and other genomes have not yet been fully explored. Examples of the kind of experiments carried out within this field are given below.

Fluorescence in situ hybridisation (FISH) has been applied with a multitude of probes of different complexity for chromosome painting (Lichter et al., 1988;

Pinkel et al., 1988) and chromosome bar coding (Lengauer et al., 1993) and has provided the most direct and rapid way to map the chromosomal localisation of DNA sequences (Lichter et al., 1990). FISH to extended chromatin fibres and single DNA strands has brought the mapping resolution down to the kilobase (kb) range offering powerful new possibilities for the generation of high resolution physical maps (Florijn et al., 1995, Weier et al., 1995).

Multicolour FISH approaches taking advantage of the combinatorial use of six fluorochromes have allowed to distinguish each of the 24 human chromosomes by a different colour (Speicher et al.; 1996, Schrock et al., 1996). FISH to extended DNA molecules has brought down the mapping resolution of this approach to the kb range offering powerful new possibilities for the generation of high resolution physical maps (Weier et al., 1995; Florijn et al., 1995).

Interphase FISH ("interphase cytogenetics"; Cremer et al., 1986) has allowed the study of numerical and structural chromosome aberrations directly in the cell nucleus.

Comparative genomic hybridisation (CGH, Kallioniemi et al., 1992, du Manoir et al., 1993; Joos et al., 1993) has provided a powerful tool to detect non-random gains and losses of DNA sequences in genomic DNA (obtained, for example from tumour specimens).

Procedures for the quantitative and automated evaluation of FISH experiments have been developed in parallel and hold the promise for fully automated optical mapping approaches in the future.

Present diagnostic and research applications range from prenatal diagnosis to postnatal clinical cytogenetics, from studies of genetic changes in cancer (du Manoir, 1995; Piper et al., 1995) to biological dosimetry (Cremer et al., 1990; Lucas et al., 1992), from comparative chromosome mapping (Wienberg et al., 1990; 1995) to studies of the 3D-organisation of genomes in situ (Manuelidis, 1990; Cremer et al., 1993). Chromosome-specific cDNA and other libraries, as well as subregional probes, for example microdissection probes, YACs, BACs, PACs, cosmids that are presently available, often do not optimally serve the needs of molecular cytogenetics applications. Several examples may serve to demonstrate the needs of improved probes:

All probes presently available for Southern blotting and FISH which are derived, for example, from cosmid, BAC, PAC and YAC libraries contain interspersed repetitive sequences. This presents a problem when probes derived from genomic DNA are hybridised to DNA on Southern blots or to chromosomes/nuclei in situ, since the interspersed repetitive sequences present in the probe DNA hybridise throughout the target DNA, i.e. to all of the DNA present on Southern blot or within all chromosomes/nuclei in situ. Thus the hybridisation to the true target sequence is obscured by background hybridisation everywhere else. To prevent non-specific hybridisation between interspersed repeat sequences of probe and target, an excess of unlabeled competitor DNA is usually included in the hybridisation mix as "blocking" agent. Southern blotting techniques usually use total human DNA for this purpose (Sealey et al, 1985) and FISH, Cot-1 DNA (Pinkel et al., 1988; Lichter et al., 1988). Cot-1 DNA is highly enriched for sequences present more than $10^4$ copies per haploid genome. However, the routine inclusion of commercial sources of Cot-1 DNA in hybridisation mixtures in excess quantities is expensive. A certain fraction of labelled, interspersed sequences will hybridise to target sequences even in the presence of excess Cot-1 DNA and lower the signal to background ratio of hybridisation signals. Thus there is an urgent need for the development of improved probes which entirely lack repetitive sequences which are shared with other chromosomes and thus impair the specificity of the probes.

In studies employing GGH to chromosomes or to DNA microarrays (Kallioniemi et al., 1992; du Manoir et al., 1993; Schena et al., 1995; Shalon et al., 1996), representational difference analysis (RDA; Lisitsyn et al., 1993) or genomic mismatch scanning (Nelson et al., 1993), it would be clearly advantageous if the DNA used for such studies would not comprise the entire complexity of a large genome, but a representative sample highly enriched in single copy or coding sequences, In multicolour FISH studies employing combinatorial probe labelling (Speicher et al.; 1996, Schröck et al., 1996), it would be advantageous if probe sets have no repetitive sequences. Usually, so many different probes have to have be hybridised a with correspondingly large amount of Cot-1 DNA, thus making hybridisations both expensive, bulky and liable to have low signal to background ratios.

In FISH studies of chromosome evolution, probes representing entire genomes, as well as chromosome or chromosomal subregions need to be enriched for sequences conserved between two species of interest to define more readily evolutionary conserved segments along chromosomes, as well as evolutionary chromosomal rearrangements in species belonging to a given class or even to different classes.

In studies of 3D in situ human genome organisation, chromosome- and chromosome region-specific paint probes containing specific subsets of sequences would be highly useful, such as complementary sets comprising coding sequences vs. non-coding sequences, "scaffold" attached sequences vs. non-attached sequences.

If a DNA probe is generated by PCR or is present within a vector, the knowledge of whose sequence facilitates PCR amplification, then the probe can be further amplified using the existing primers. Some complex probe sets are amplified using a universal PCR amplification protocol. This means that when the probe set is first selected, usually from an amount of DNA corresponding from a small number of nuclei, it is amplified in a way that maximises amplification of all DNA fragments. There are at least two ways of doing this: DOP-PCR and linker-adapter PCR.

Since 1992, universal DNA amplification procedures have been introduced that allow the amplification of any DNA sources employing primers which contain a stretch of random base pairs and another stretch with a specific DNA sequence (Telenius et al., 1992, Bohlander 1992). The method described by Telenius et al., (1992) termed degenerate oligonucleotide-primed (DOP)-PCR is well established in our laboratories, with the same oligonuctide [SEQ ID NO.: 1] ("6MW", 5'-CCG ACT CGA GNN NNN NAT GTG G-3') and conditions as Telenius et al., (1992). During the first five PCR cycles, which are performed under conditions of lower stringency (i.e. a low annealing temperature), the primer part comprising the random ($N_6$) sequence can hybridise to many sites of any complex DNA source. Subsequent cycles performed under stringent conditions (i.e. a higher annealing temperature) should, in theory, allow the specific, further amplification of those DNA fragments in which the specific primer sequence has been incorporated during the first amplification cycles.

Linker-adapter PCR strategies involve the generation of specific target sequences at the end of DNA fragments which hybridise to unique primer pairs. This approach allows the amplification and reamplification of complex sources of DNA such as DNA from microdissected chromosomes, chromosome arms and chromosome bands (Lüdecke et al., 1989; Vooijs et al., 1993).

Subtractive hybridisation involves the hybridisation of two sets of DNA molecules, the source DNA and the subtractor DNA. Usually, the contents of the these two DNA sets overlap. The relative amounts of source and subtractor DNA can be altered to drive the hybridisation kinetics to favour either positive or negative selection. Positive selection, in which the number of source molecules is usually greater, would involve isolation of subtractor-homologous source DNA. Negative selection, in which the number of subtractor molecules is greater, would involve isolation of subtractor-nonhomologous source DNA. In addition, the selected DNA can be put through more round (s) of selection to further improve the selection process. Subtractive hybridisation was first used to clone the differences between two overlapping pools of cDNAs; double-stranded hybrid molecules were separated from free single-stranded cDNAs by chromatography through hydroxylapatite (Kurtz and Feigelson, 1977; Affara and Daubas, 1979; Timberlake, 1980). This enabled only negative selection. With the substitution of biotin-labelling of the subtractor DNA followed by avidin-affinity capture and release techniques, it became possible to both positively and negatively select subsets of source DNA (Welcher et al., 1986). This technique was further improved by the addition of a post-selection inter-Alu-PCR amplification step (Rounds et al., 1995).

The concept of removing repetitive sequences from chromosome-specific libraries employed for the FISH-visualisation of entire chromosomes and chromosomal sub-regions by affinity chromatography procedures and alternatively to suppress the undesired hybridisation of hapten-labelled repetitive probe sequences with Cot-DNA fractions as blocking agents was first tested by T. Cremer and P. Lichter when they worked together with David C. Ward at the Dept. of Genetics, Yale University (1986–1988). Copper chelation affinity chromatography, a well known procedure for the purification of proteins, had already been modified there for use in the enrichment of specific DNA sequences from complex DNA sources (Welcher et al., 1986).

The following strategy to produce a human chromosome 21 "paint" probe library depleted in interspersed repetitive sequences, as well as other repetitive sequences cross-hybridising to other acrocentric chromosomes was tested at that time. In the following strategy, source DNA is represented by a chromosome 21 paint probe and the subtractor by biotinylated and $^3$H-labelled sequences representing flow sorted chromosomes 13 and 18, and cloned repetitive sequences. These subtractor sequences were used in excess (50 fold) and mixed with chromosome 21 subtractor sequences end-labelled with $^{32}$P. The radioactive labelling was performed as a simple means to follow the presence of subtractor and source sequences and the intended fractionation of the latter. Following hybridisation of subtractor and source DNA in suspension, and incubation with avidin, the hybridisation mixture was subjected to copper chelation chromatography. The affinity of the columns for avidin was used with the intention of removing all biotinylated subtractor DNA sequences and subtractor DNA-source DNA hybrids ($^3$H labelling was used to monitor the bound fraction and possible leakage of the column). The expected enrichment of chromosome 21-specific, $^{32}$P-labelled source sequences in the flow-through fraction (negative selection) was monitored by a filter hybridisation assay with spots representing the various components of the subtractor DNA and the chromosome 21 source DNA. After several cycles, a strong increase in the intensity of the chromosome 21 spot demonstrated the enrichment of chromosome 21-specific sequences in the flow-through fraction.

However, a major drawback of this approach resulted from the fact that the columns retained the large majority but less than 100% of the biotinylated subtractor DNA. This means that the fraction of excess biotinylated subtractor sequences recovered in the flow-through fraction reflected a total amount similar or even higher than the amount of the purified source DNA. This fraction of subtractor DNA which leaked into the flow through fraction made the total DNA recovered in the flow through fraction at this stage of the development useless as a probe for immediate molecular cytogenetic applications, in spite of the experimentally-demonstrated enrichment of chromosome 21 unique sequences. As a result of this leakage, repetitive sequences, which were depleted from the 21 library probe, were replaced in the flow-through fraction to a significant extent by repetitive sequences from the subtractor DNA. Accordingly, this attempt to prepare a 21-specific chromosome paint probe which could be used without Cot-1 DNA in the hybridisation mixture failed, i.e. FISH experiments of the resulting probes to metaphase spreads did not yield a specific painting of chromosome 21, but still visualised the entire chromosome complement. In the case of positive selection (i.e. subsequent elution of a fraction bound to the column) the situation is even worse, since all subtractor DNA bound to the column will be eluted together with the subtractor-source DNA hybrids, using this approach.

Two recent publications have used two modifications to the previously-used subtractive hybridisation protocol to positively select chromosome-specific cDNAs (Chen-Liu et al., 1995; Rouquier et al., 1995). Firstly, source cDNA libraries were made universally amplifiable by the addition of linker-adapter ends. Using single chromosome libraries as subtractor DNA, chromosome-specific cDNAs were PCR-amplified after positive selection. A further step was achieved by using streptavidin-coated magnetic beads for affinity chromatography, hence reaction volumes were kept to a minimum. In addition, single-stranded source molecules could be released from immobilised subtractor molecules by alkaline denaturation after stringent washes, thus further improving the purity of the released source DNA. When two consecutive rounds of positive selection were employed, this led to a selection of chromosome-specific cDNA. However, the method described in these two publications have used Cot-1 DNA to suppress any repeat-repeat hybridisation within or between subtractor and source DNA (Chen-Liu et al., 1995; Rouquier et al., 1995). This makes the process of positive selection more complicated and makes negative selection almost impossible (the unlabelled Cot-1 DNA would pass through into and heavily contaminate the supernatant to be amplified for negative selection).

Thus, the technical problem underlying the present invention is to provide a novel and generally useful strategy to fractionate and purify DNA from entire genomes, as well as from chromosome-specific or chromosome segment-specific DNA probes. This approach can be used to develop probe sets for molecular cytogenetics with novel and different characteristics, such as probe sets comprising coding sequences, expressed sequences, sequences conserved between two distantly-related species, etc. Such probe sets will be generated in a way that they can be reamplified and used without any additional "blocking" agents such as Cot-1 DNA. These novel probe sets will become highly useful in diagnostic and research settings.

The above technical problem is achieved by providing the embodiments characterized in the claims.

In particular, there is provided a method of purifying specific DNA molecules, comprising the steps of
(a) mixing a set of DNA molecules as source DNA containing said specific DNA molecules as a subset, with a set of molecules as subtractor having substantially
    (i) an affinity for the subset, or
    (ii) no affinity for the subset,
(b) performing a binding reaction between source DNA and subtractor in solution,
(c) separating the subtractor which is present unbound or bound to source DNA, by binding the subtractor to a matrix material containing compounds having an affinity to the subtractor, from the reaction mixture, and
(d) recovering said subset which is either
    (i) bound to the subtractor, or
    (ii) not bound to the subtractor.

In the case of the feature of step (a) (ii), the subtractor having substantially no affinity for the subset, exhibits an affinity for substantially all other DNA molecules contained in the source DNA.

The recovered subset obtained in step (d) (i) derives from a "positive selection" using preferably an excess of source DNA. The recovered subset obtained in step (d) (ii) derives from a "negative selection" using preferably an excess of subtractor.

In a preferred embodiment, the subtractor is a set of DNA molecules and the binding reaction in step (b) is a hybridisation. In this aspect, the hybridisation may be performed by denaturing source DNA and subtractor mixed together in a buffer containing 0.075 M to 1.5 M NaCl, at 90 to 100° C. for 1 to 10 minutes and reannealing at 60 to 70° C. for 5 to 48 hours. Alternatively, the hybridisation may be performed by denaturing source DNA and subtractor mixed together in a buffer containing 40 to 70% v/v formamide, 0.03 M to 0.75 M NaCl, at 60 to 80° C. for 1 to 10 minutes and reannealing at 30 to 50° C. for 5 to 48 hours.

In a further preferred embodiment of the present invention, the source DNA is a DNA probe used in FISH. The source DNA may comprise DNA of a defined function or a repeat-free chromosane-specific library. Examples are cDNA, CpG islands, scaffold-attached DNA and DNA of a defined replication time.

The subtractor may be a set of labelled molecules such as DNA molecules, wherein the percentage of labelling is $\geq 90\%$, more preferred $\geq 95\%$, and most preferred $\geq 97\%$ such 99.5%. The molecules are labelled e.g. with biotin or digoxygenin, wherein the label or labelling method are not specifically restricted and any label or labelling method known in the art can be used within the present invention. In a preferred embodiment of the present invention, the subtractor is Cot-1 DNA.

Cot DNA means a double stranded DNA formed after a mixture of DNA molecules, at a known concentration of DNA and salt, which has been denatured and reannealed until a certain value of the product of molar concentration ($C_o$) and time (t) has been reached. Cot-1 DNA represents the double stranded DNA formed after DNA has been denatured and reannealed until the product of molar concentration and time is 1, and represents sequences repeated more than 10,000 times per haploid human genome.

The subtractor may comprise a repeat-free chromosome-specific library or DNA of a defined function. Examples are cDNA, CpG islands, and scaffold-attached DNA.

Preferred embodiments of the present invention with respect to source DNA and subtractor are as follows:
  the source DNA comprises repeat-free DNA from one species and the subtractor comprises repeat-free DNA from another species;
  the source DNA comprises repeat-free DNA from one species or DNA sequences shared between two different species, and the subtractor is a repeat-free chromosome-specific library from another species;
  the source DNA is a repeat-free chromosome-specific library from one species, and the subtractor comprises repeat-free DNA from another species or DNA sequences shared between two different species;
  the source DNA comprises repeat-free DNA from one particular tissue and/or developmental stage, and the subtractor comprises repeat-free DNA of a defined function from another particular tissue and/or developmental stage of the same organism.

The matrix material used in step (c) is not specifically restricted, and any matrix material known in the art can be used within the present invention. The compounds contained in the matrix material are preferably immobilized to the matrix material. In a preferred example, the matrix material contains streptavidin such as streptavidin-conjugated magnetic beads.

In another embodiment of the present invention, the source DNA contains thymidine analogues, the subtractor contains anti-thymidine analogue antibodies, and the matrix material contains compounds capable of binding to the anti-thymidine analogue antibodies. Alternatively, the source DNA contains bromode-oxyuridine (BrdU), the subtractor contains anti-BrdU antibodies, and the matrix material contains compounds capable of binding to the anti-BrdU antibodies. Prior to step (a) of the method according to the present invention, the source DNA may be subjected to PCR such as DOP-PCR. In a preferred embodiment, prior to step (a), the source DNA is subjected to a further round of PCR with a second primer whose 5'-portion comprises a sequence of nucleotides not present in the DOP primer, and whose 3'-portion consists of a number of the non-random nucleotides from the 5'-end of the DOP-prer, Preferably, the DOP-PCR primer ("first primer") has the following sequence [SEQ ID NO.: 1]:

5'-CCG ACT CGA GNN NNN NAT GTG G-3'
wherein N may be any nucleotide.

Further, the second primer may have the following sequences [SEQ ID NOS: 2–3]:
   5'-CTA CTA CTA CTA CCG ACT CGA G-3', or
   5'-TGA TCA CGC TAC CCG ACT CGA G-3'.

After step (d) of the method according to the present invention, the recovered subset may be subjected to PCR. Further, steps (a) to (d) are repeated at least once using each recovered subset obtained in step (d) as source DNA in step (a).

The subset obtained according to the method of the present invention may be used as a probe for DNA-DNA hybridisations such as Southern blotting or FISH.

A further subject of the present invention relates to a DNA probe containing less than 2% Cot-1 DNA.

The source DNA are preferably selected from probes cloned in vectors, complex probe sets created by PCR amplification and/or microdissection or flow-sorting, repeat-free chromosome-specific library, repeat-free genomic DNA purified from cells with tymidine analogues incorporated into R- or G-bands, early or late replicating genomic DNA and repeat-free genomic DNA. The source DNA originates from any living material such as plants, fungi, bacteria, animals and humans, and specific tissues or cells thereof. Examples are: Humans, mice, sheep, cows, horses, pigs, goats, rabbits, ostriches, chickens, pigeons, maize, wheat, rice, barley, oats, rye, sorghum, millet, and yeasts such as *Saccharomyces cerevisiae, Schizosaccharomyces pombe*.

The Figures show:

FIG. 1 is a general set-up of one preferred embodiment of the present invention. a, General schematic diagram, and b, as applied to the removal of repetitive DNA from FISH probe sets. PCR-amplifiable probe sets (acting as "source" DNA) are hybridized in solution with biotinylated Cot-1 DNA (acting as "subtractor"DNA). Cot-1:Cot-1 and Cot-1 probe set hybrids are removed using streptavidin-magnetic bead affinity chromatography, leaving the repeat-depleted sub-fraction of the probe set (negative selection) to be purified and PCR-amplified.

FIG. 2 is a fluorescence in situ hybridization of probe sets (A, B, 15*q* library; C, D, genomic DNA) without Cot-1 DNA, after two rounds of repeat depletion. Images were taken directly through the microscope with a conventional camera; no image processing was employed. A, C: DAPI counterstaining; B, D: biotin-labelled, avidin-FTTC-detected depleted probe sets. In B, two metaphase chromosomes (center, indicated with arrowheads in A) and two interphase chromosomes 15*q* (left) have been painted. Background hybridization to other, nontarget chromosomes is relatively low compared to the target chromosomes, indicating that sufficient repeats have been removed from the probe set as are necessary for Cot-1-free FISH. In D, the dentromeric satellite DNA of chromosome 1 (arrowheads), the heterochromatin of the Y chromosome, plus some non-hybridising centromeres (arrows) are indicated as examples of regions of repetitive DNA that have been effectively removed from the genomic DNA probe set.

According to the present invention, a preferred embodiment is that ≧95% of subtractor molecules are labelled such as biotin-labelled; any unlabelled molecules will not be captured by the matrix material such as streptavidin-magnetic beads. In the case of positive selection, this would result in the loss of a subset of subtractor-homologous source DNA sequences. In the case of negative selection, this would lead to the contamination (dilution) of the source DNA with subtractor DNA and the possibility that a subset of unwanted, subtractor-homologous source DNA sequences were not captured by affinity binding and would therefore also be amplified by a resulting PCR amplification, thus making selection incomplete.

In one preferred embodiment of the present invention, stringent PCR amplification is central to the claimed method. If PCR reactions are not sufficiently stringent, contaminating subtractor DNA may be co-amplified with source DNA after recovering in step (d) of the method according to the present invention. Sequence-specific PCR and linker-adapter (universal) PCR are stringent enough in this respect. However, although the universal DOP-PCR technique has the advantage over Linker adapter PCR that it requires no pre-ligation of linker molecules, based on the fact that even when the so-called "stringent" (high annealing temperature) DOP-PCR cycles are used to reamplify DOP-PCR probe libraries, amplification is not completely restricted to DNA molecules which carry DOP primer sequences at their ends. Thus, a certain likelihood exists that contaminating subtractor sequences could still be amplified. DOP-PCR is the most widely-used technique used generate complex FISH probes. From the starting material of flow-sorted or microdissected genomes, genome subsets, chromosomes and chromosome subsets down to the level of single chromosome bands, DOP-PCR is used as a universal PCR amplification technique to generate amplifiable probe sets. It is also the ideal protocol to convert probes that are not already PCR-amplified into PCR-amplified probe sets, thus eliminating the need for cloning in vectors.

In one preferred embodiment of the present invention, a new DOP-PCR primer is provided to exclude the degenerate sequences from the priming reaction of PCR amplification. This was done by taking the first ten, specific nucleotides from the "6MW" primer and adding twelve more nucleotides [SEQ ID NO.: 2] to the 3' end. The new primer (5'-CTA CTA CTA CTA CCG ACT CGA G-3', also called "CTA$_4$DOP". This primer was used in a modified DOP-PCR reaction to effectively add the CTA$_4$ sequence onto all source DNA molecules before the start of step (a) of the method according to the present invention. Tests showed that using a slightly modified, stringent set of CTA$_4$DOP-PCR cycles that no amplification of contaminating sequences occurred.

While previous studies on PCR-assisted affinity capture implied and performed only positive selection of source DNA (Chen-Liu et al., 1995 and Rouquier et al., 1995) to a certain extent, the method of the present invention can be also used successfully for negative selection. For example, after separation of e.g. biotin-labelled, subtractor-subtractor and subtractor-source molecules, all subtractor-nonhomologous source sequences should be left in the supernatant. One extra step of e.g. streptavidin-magnetic particle affinity binding with this negatively-selected supernatant fraction is performed to ensure the capture of any remaining subtractor sequences. This effectively ensures that >99.5% of all subtractor molecules have been removed during negative selection.

Using the method according to the present invention, repetitive DNA can be successfully removed from complex probe pools (see FIG. 2). If all subtractor and source DNA sets (apart from those involved in the actual process or repeat removal) pre-treated in this way, prehybridisation of either DNA with Cot-1 DNA can be entirely avoided and negative selection would be made much easier.

The general set-up of one preferred embodiment of the present invention is illustrated in FIG. 1a. The subtractor DNA comprises the sequences for which positive or negative selection is required. The source DNA comprises the probe set from which to select either subtractor-homologous sequences (positive selection) or subtractor-nonhomologous sequences (negative selection). The source DNA probe or probe set is first amplified using PCR methods, the most widely-used of which will be the above defined DOP-PCR technique using the $CAT_4$ DOP-primer. The subtractor DNA is labelled (e.g. with biotin using Biotin Chem-Link, Boehringer Mannheim). Source DNA is hybridised to subtractor DNA then mixed with streptavidin-magnetic particles. In positive selection, source DNA molecules containing subtractor-homologous sequences are purified using high stringency washes followed by alkali denaturation and universal PCR. In negative selection, source DNA molecules containing no subtractor-homologous sequences are purified using a further incubation with streptavidin-magnetic particles followed by universal PCR. This selected DNA can be tested using normal hybridisation techniques and subjected to further rounds of selection if required. In this respect, it has been demonstrated that as many as five consecutive reamplifications of a DOP or linker-adapter chromosome library do not apparently decrease the complexity of the probe set as tested by FISH.

The present invention makes possible the development of novel probes with many different applications in diagnostic and research settings. In addition, reamplifiable probes allow both small and large scale probe applications.

In the following, preferred embodiments of the present invention are summarized:

| (1) Preparation of repeat-free PCR-amplifiable DNA probes | |
|---|---|
| Type of selection: | Negative |
| Source DNA: | PCR-amplified DNA probes., e.g. probes cloned in vectors such as phages, cosmids, YACs, BACs, PACs; complex probe sets created by PCR amplification and/or microdissection or flow-sorting, e.g. band, arm or whole chromosome-specific probe sets. |
| Subtractor DNA: | Biotin-labelled Cot-1 (or higher Cot) DNA |
| Desired DNA: | PCR-amplified DNA from the supernatant fraction after streptavidin-magnetic particle affinity chromatography. |
| Expected characteristics of new probe sets: | Repeat-free probe sets that require little or no suppression before DNA-DNA hybridisation and which achieve low levels of background hybridisation combined with the desired specificity. |

Applications: Production of repeat-free, PCR-amplifiable probe sets for DNA-DNA hybridisations such as Southern blotting or in situ hybridisation of human and other species for diagnostic and research use. Major examples are PCR-amplified arm- or whole-chromosome probe sets for multi-colour FISH assays, genomic DNA for comparative genomic hybridisation to chromosomes or matrices or in representational difference analysis (RDA; Lisitsyn et al., 1993) or genomic mismatch scanning (2–20 kb; Nelson et al., 1993).

| (2) Preparation of chromosome-specific functionally-defined DNA probes | |
|---|---|
| Type of selection: | Positive |
| Source DNA: | Repeat-free PCR-amplified chromosome-specific library (see embodiment 1) |
| Subtractor DNA: | (Repeat-free and/or PCR amplified) functionally-defined subsets of DNA, e.g. cDNA libraries, CpG island libraries, scaffold-attached regions (SARs), DNA of defined replication time. |
| Desired DNA: | PCR-amplified DNA from the bound fraction after streptavidin-magnetic particle affinity chromatography. |
| Expected characteristics of new probe: | Chromosome-specific DNA of a defined function. |

Note: Source and subtractor DNAs are interchangeable for this embodiment.

Applications: Detection of metaphase and interphase chromosome subregions with a defined function, e.g. to detect regions containing a high density of (active) genes. Screening of cosmid, BAC, PAC and YAC libraries for expressed sequences.

| (3) Preparation of genomic probes enriched in evolutionary conserved sequences | |
|---|---|
| Type of selection: | Positive |
| Source DNA: | Repeat-free, PCR-amplified genomic DNA from one species (see embodiment 1) |
| Subtractor DNA: | Repeat-free genomic DNA from another species |
| Desired DNA: | PCR-amplified DNA from the bound fraction after streptavidin-magnetic particle affinity chromatography. |
| Expected characteristics of new probe: | Sequences conserved between the two genomes; the extent of conservation depends on the stringency conditions used for hybridisation in suspension. |

Applications: FISH of the probe obtained from one species to metaphase spreads from the other species provides a tool for the comparative physical mapping of highly conserved sequences. Such an approach will be particular interesting for distantly-related species.

| (4) Preparation of chromosome-specific probes enriched in evolutionary-conserved sequences | |
|---|---|
| Type of selection: | Positive |
| Source DNA: | Repeat-free, PCR-amplified DNA from one species or DNA sequences shared between two different species (see embodiment 3) |
| Subtractor DNA: | Repeat-free chromosome-specific library from another species |
| Desired DNA: | PCR-amplified DNA from bound fraction after streptavidin-magnetic particle affinity chromatography |
| Expected characteristics of new probe: | Chromosome-specific DNA from the first species highly enriched for evolutionary-conserved sequences |

Note: Source and subtractor DNAs are interchangeable for this embodiment.

Applications: These probes should become highly useful for comparative chromosome mapping. For example, FISH of this probe to metaphase chromosomes of the second should light up the homologous segments. Fractionation of all chromosome-specific paint probes of a given species, e.g. Human, in this way should provide tools for comparative mapping even beyond the mammalian order. In combination with multicolour FISH the rapid establishment of comparative chromosome maps even for very distantly-related species will become feasible.

---

(5) Selection of DNA molecules exclusive to one tissue or developmental stage

Type of selection: Positive

Source DNA: Repeat-free, PCR-amplified, functionally-defined subsets of DNA (see embodiment 2) from one or more tissues or one or more developmental stages of an organism.
Subtractor DNA: (Repeat-free) PCR-amplified, functionally-defined subsets of DNA (see embodiment 2) from different tissues or developmental stages of the same organism.
Desired DNA: PCR-amplified DNA from bound fraction after streptavidin-magnetic particle affinity chromatography.
Expected characteristics of new probe: Tissue-specific or developmental stage-specific DNA.

Note:
Source and subtractor DNAs are interchangeable for this embodiment.

---

Applications: Sets of DNA molecules can be used to isolate genes active in particular tissue(s) or developmental stage(s).

The following examples illustrate further the present invention.

Biotinylation of Cot-1 DNA

Cot-1 DNA (Gibco BRL or made in our lab) was labelled with biotin using a Biotin Chem-Link kit (Boehringer Mannheim). Manufacturer's instructions were followed except that the reaction was scaled up and 25 µg (25 µl) DNA was labelled with 25 µl Biotin Chem-Link and the volume made up to 75 µl with distilled water. After labelling (30 min at 85° C.), 25 µl "Stop Buffer" (provided with the Biotin Chem-Link kit) was added and the products cleaned using standard Sephadex G50 columns (Sambrook et al. 1989) or BioRad Micro Bio-Spin 30 Tris columns.

Preparation of Source DNA

All PCR reactions were performed in the following buffer (modified slightly from Telenius et al. 1992): 1×Taq DNA polymerase buffer (50 mM KCl, 10 mM Tris.HC pH 8.3, Perkin Elmer), 2 mM $MgCl_2$, 0.2 mM of each dNTP, 1.7 µM primer [SEQ ID NO.: 1] 6MW (5'-CCG ACT CGA GNN NNN NAT GTG G-3'), 100 ng template DNA and 5 units of Taq DNA polymerase (Pharmacia), in a final volume of 100 µl. Screw-capped tubes were used for amplification (using a Biomed Thermocycler 60); no oil overlay was used. The first stage of probe preparation was DOP-PCR (Telenius et al. 1992). PCR conditions were as follows: 96° C. for 5 min, followed by the addition of Taq polymerase; 5 cycles of 96° C. for 1 min, 30° C. for 1.5 min, 72° C. for 3 min with 3 min time ramp from 30° C. to 72° C.; 35 cycles of 96° C. for 1 min, 62° C. for 1.5 min, 72° C. for 3 min, with the addition of 1 sec. per cycle to the extension time. PCR products were purified using a QIAquick PCR purification kit (Qiagen) according to manufacturer's instructions. The second stage involved amplification of 100 ng of products from the first PCR reaction with a newly-designed primer [SEQ ID NO.: 2] "$CTA_4DOP$" (5'-CTA CTA CTA CTA CCG ACT CGA G-3'). PCR conditions were as follows: 96° C. for 5 min, followed by the addition of Taq polymerase; 4 cycles of 96° C. for 1 min, 48° C. for 1.5 min, 72° C. for 3 min; 17 cycles of 96° C. for 1 min, 55° C. for 1.5 min, 72° C. for 3 min, with the addition of 1 sec. per cycle to the extension time. DNA was purified as above.

Hybridisation of Biotinylated Cot-1 and Source DNA.

200 ng source DNA was added to a 50-fold excess (10 µg) of biotin-labelled Cot-1 DNA. The DNAs were precipitated together by addition of 1/10 volume 3M sodium acetate followed by a standard ethanol precipitation. Dried mixtures of biotinylated Cot-1 DNA and source DNA were redissolved in 100 µl 6×SSC/0.1% SDS, denatured by boiling for 10 min and hybridised at 65° C. overnight (Rouquier et al, 1995).

Selection of Unbound Source Molecules Using Negative Selection with Streptavidin Affinity Chromatography Prior to streptavidin-magnetic particle affinity chromatography, the two hybridised DNAs were cooled to room temperature. 2 mg (200 µl) streptavidin magnetic particles (Boehringer Mannheim) were prepared according to manufacturers instructions and resuspended in 125 µl of 10 mM Tris.HCl, pH 8.0/1 mM EDTA pH 8.0/2 M NaCl (2×binding and washing buffer). 100 µl streptavidin magnetic particles were added to 100 µl hybridised DNA mixture and incubated at room temperature for 30 min with axial rotation. Tubes were then applied to a magnetic particle separator (Boehringer Mannheim) for 3 min and the supernatant gently removed. This supernatant was added directly to the remaining, unused magnetic particles with buffer freshly removed, and incubated with axial rotation as above. The second supernatant (200 µl) was removed and DNA purified using a QIAex II kit (Qiagen) according to manufacturers instructions, and resuspended in 25 µl TE (10 mM Tris.HCl, pH 8.0/1 mM EDTA pH 8.0).

Reamolification of Selected Source DNA.

5 µl (approximately 30 ng) of purified, selected source DNA was subjected to PCR with the primer $CTA_4DOP$ as above, without the four low annealing temperature cycles. DNA was purified as for previous PCR amplifications. At this stage, one round of selection was complete. If a further round of selection was required, this DNA would be treated as source DNA and subjected once more to hybridisation with Cot-1, affinity chromatography and PCR.

Fluorescence in situ Hybridisation

Probes were labelled with biotin-16-dUTP (Boehringer Mannheim) using standard nick translation procedures. Hybridisation to metaphase chromosomes was carried out as follows: slides were denatured for 2 min at 72° C. in 70% formamide/0.6×SSC/pH7.0; thereafter slides were put through an ice cold ethanol series (70%/90%/100%) and air-dried. 250 ng of probe together with 50 µg sonicated salmon testis DNA (Sigma) were ethanol precipated, dried, and redissolved in 10 µl hybridisation solution (50% formamide/1×SSC/10% dextran sulphate). Slides were denatured in 70% formamide/2×SSC for 2 min at 72° C. and put through another ethanol series; probes were denatured at 75° C. for 5 min and not reannealed. Probes were then added to slides, covered by an 18×18 mm coverslip, sealed with rubber cement and hybridised at 37° C. overnight. Slides were washed 3×5 min in 50% formamide/I×SSC and another 3×5 min in 0.1×SSC at 60° C. Thereafter, they were incubated for 30 min with 4% BSA/2×SSC/0.1% TWEEN 20 (monolaurate, non-ionic detergent) at 37° C. (a blocking step to reduce background). Slides were then washed briefly in 4×SSC/0.1% TWEEN 20 then incubated with 1 ng/µl avidin-FITC (Vector) in 100 µl 4×SSC/0.1% TWEEN 20 for 30 min at 37° C. Slides were then washed 3×2 min in 4×SSC/0.1% TWEEN 20 at 45 ° C., and incubated in 2.5 ng/µl biotinylated anti-avidin (Vector) in 100 µl 4×SSC/ 0.1% TWEEN 20 for 30 min at 37° C. Slides were washed and incubated once more with avidin-FITC and washed again, as above. Chromosomes were counter-stained in 20 ng/ml DAPI in 4×SSC/0.1% TWEEN 20 for 5 min, rinsed in distilled water and mounted in Vectashield antifade mounting medium (Vector).

Fluorescence Microscopy

A Zeiss Axiophot microscope equipped with a 100 W mercury lamp was used with DAPI and FITC Chroma filters (AHF Tübingen, Germany). All images were acquired with a Plan Neofluar 100×/1.3 oil immersion lens. Photomicrographs were taken directly through the microscope with Kodak Ektachrome 400 film; no image processing was employed.

Figure 1B:
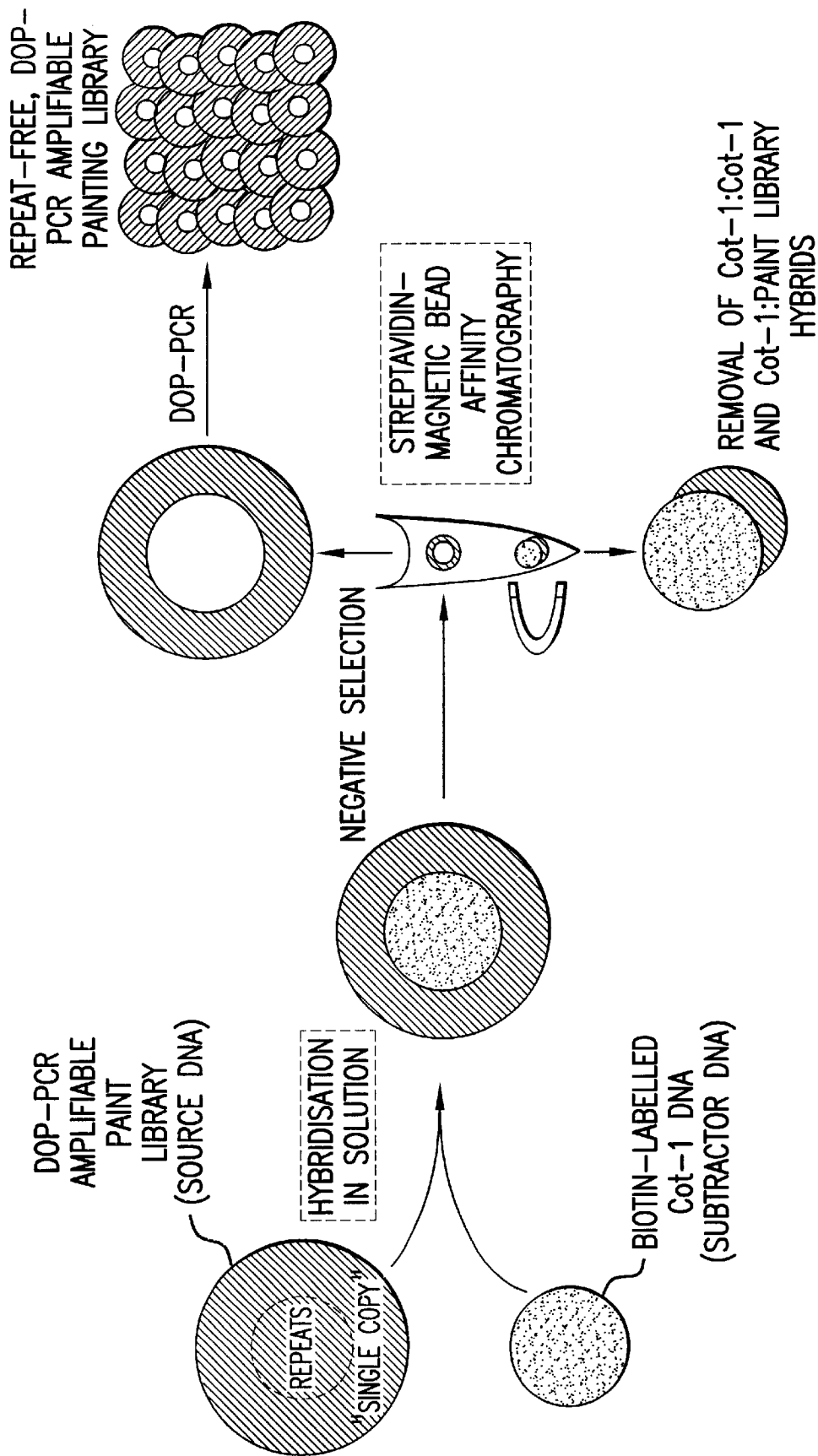
Figure 2A:
Figure 2B:
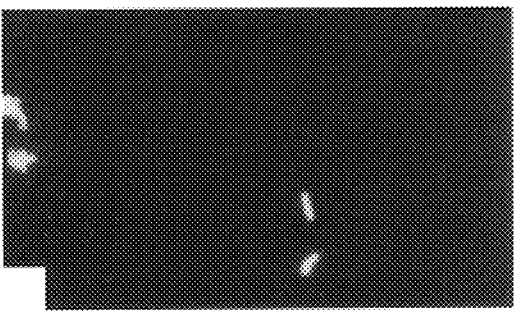
Figure 2C:
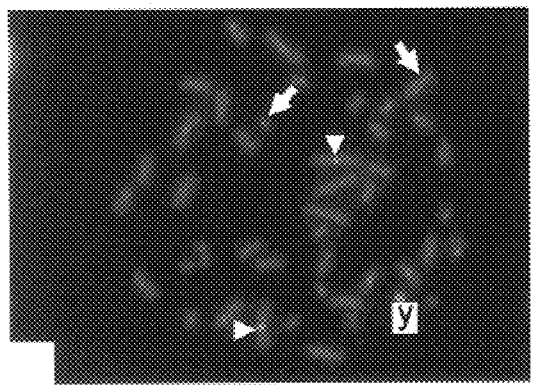
Figure 2D:
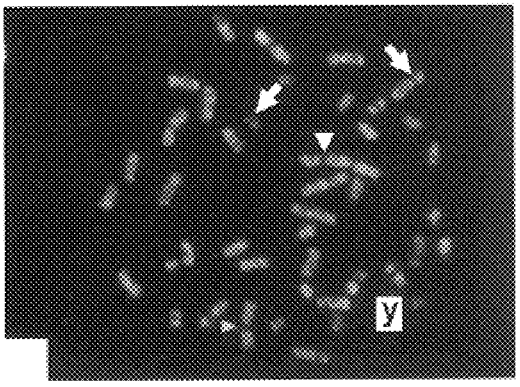

The approach outlined above (using two rounds of negative selection) is successfully used to remove repetitive DNA from probes (and probe sets) which formerly were or were not PCR-amplified (FIG. 1b). Of the already DOP-PCR-amplified probe sets, both single arm painting probes (e.g. human chromosome 15q, see FIG. 2) or whole chromosome painting probes (e.g. human chromosome 6, results not shown) habe been repeat-depleted. Further, genomic DNA after first making it amplifiable with our stringent DOP-PCR primers (FIG. 2), has been repeat-depleted. The same was done with PAC and YAC clones (results not shown). FISH of the selected probes without Cot-1 DNA was used to demonstrate the effectiveness of the selection technique (FIGS. 2a,b). Hybridisation of the depleted chromosome 15q-specific probe library showed a strong hybridisation to chromosome 15q only (FIGS. 2c,d). Hybridisation of the treated genomic DNA showed a strong hybridisation to all regions of the genome except for those known to exclusively contain repetitive DNA (e.g. centromeric and Y-specific satellite DNA (FIG. 2b). This has demonstrated that not only can make a range of FISH probes PCR-amplifiable, but also that both interspersed (e.g. Alu repeats present on 15q) and clustered repeats (e.g. centromeric and heterochromatic satellite DNA present in genomic DNA) can be removed from such probes.

References

Affara N. and Daubas, P. (1979) Dev. Biol. 72, 110–125.

Bohlander S K, Espinosa R III, LeBeau M M, Rowley J D, Diaz M O (1992) A method for the rapid sequence—independent amplification of microdissected chromosomal material. Genomics 13: 1322–1324

Chen-Liu L W, Huang B C, Scalzi J M, Hall B K, Sims K R, Davis L M, Siebert P D and Hozier J C (1995) Selection of hybrids by affinity capture (SHAC): a method for the generation of cDNAs enriched in sequences from a specific chromosome region. Genomics 30: 388–3902

Cremer T, Landegent J, Brückner A, Scholl H P, Schardin M, Hager H D, Devilee P, Pearson P, Ploeg van der M (1986) Detection of chromosome aberrations in the human interphase nucleus by visualization of specific target DNAs with radioactive and non-radioactive in situ hybridization techniques: diagnosis of trisomy 18 with probe L1.84. Hum. Genet. 74:s 346–352

Cremer T, Popp S, Emmerich P, Lichter P, Cremer C (1990) Rapid metaphase and interphase detection of radiation-induced chromosome aberrations in human lymphocytes by chromosomal suppression in situ hybridization. Cytometry 11: 110–118

Cremer T, Kurz A, Zirbel R, Dietzel S, Rinke B, Schrock E, Speicher M R, Mathieu U, Jauch A, Emmerich P, Scherthan H, Ried T, Cremer C and Lichter P (1993) The role of chromosome territories in the functional compartmentalization of the cell nucleus. Cold Spring Harbor Symp. Quant. Biol. 58: 777–792.

Cremer T, Dietzel S, Eils R, Lichter P, Cremer C (1995) Chromosome territories, nuclear matrix filaments and interchromatin channels: a topological view on nuclear architecture and function. Kew Chromosome Conference IV (Ed. P. E. Brandham and M. D. Bennett). Publisher: Royal Botanic Gardens Kew, U.K., pp 63–81

Drouin R, Lemieux N, Richer C-L (1994) High-resolution replication bands compared with morphologic G- and R-bands. Adv Hum Genet (Hirschhorn K, Harris H, eds) Plenum Press, New York, pp 47–115 du Manoir S, Schrock E, Bentz M, Speicher M R, Joos S, Ried T, Lichter P, Cremer T (1995) Quantitative analysis of comparative genomic hybridization. Cytometry 19: 27–41

Florijn R J, Bonden L A J, Vrolijk H, Wiegant J, Vaandrager J W, Baas F, Dunnen den J T, Tanke H J, Ommen van G J B, Raap A K (1995) High-resolution DNA Fiber-FISH for genomic DNA mapping and colour bar-coding of large genes. Human Molecular Genetics 4: 831–836.

Guan X-Y, Meltzer P S, Trent J M (1994) Rapid generation of whole chromosome painting probes (WCPs) by chromosome microdissection. Genomics 22: 101–107.

Joos S, Scherthan H, Speicher M R, Schlegel J, Cremer T, Lichter P (1993) Detection of amplified DNA sequences by reverse chromosome painting using genomic tumor DNA as probe. Hum Genet 90: 584–589

Kallioniemi A, Kallioniemi O P, Sudar D, Rutovitz D, Gray J W (1992) Comparative genomic hybridization for molecular cytogenetic analysis of solid tumors. Science 258: 818–821

Kurtz D. and Feigelson P. (1977) Proc. natl. Acad. Sci. USA 74, 4791–4795.

Lichter P, Tang C C, Call K, et al., (1990) High resolution mapping of human chromosome 11 by in situ hybridization with cosmid probes. Science 247: 64–69

Lichter P, Cremer T, Borden J, Manuelidis L and Ward D C (1988) Delineation of individual human chromosomes in metaphase and interphase cells by in situ suppression hybridization using recombinant DNA libraries. Hum. Genet. 80: 224–234.

Lucas J N, Awa A A, Straume T, Poggensee M, Kodama Y, Nakano M, Ohtaki K, Weier H U, Pinkel K, Gray J W, Littlefield G (1992) Rapid translocation frequency analysis in humans decades after exposure to ionizing radiation. International Journal of Radiation Biology 62: 53–63.

Lisitsyn N, Lisitsyn N, Wigler M (1993) Cloning the differences between two complex genomes. Science 259:946–951.

Lüdecke H-J, Senger G, Claussen U, Horsthemke B (1989) Cloning defined regions of the human genome by microdissection of banded chromosomes and enzymatic amplification. Nature 338: 348–350.

Manuelidis L (1990) A view of interphase chromosomes. Science 250:1533–40.

Nelson S F, Mc Cusker J H, Sander M A, Kee Y, Modrich P, Brown P O (1993) Genomic mismatch scanning: a new approach to genetic linkage mapping Nature Genomics 4, 11–18.

Pinkel D, Landegent J, Collins C, Fuscoe J, Segraves R, Lucas J, Gray J W (1988) Fluorescence in situ hybridization with human chromosome-specific libraries: detection of trisomy 21 and translocations of chromosome 4. Proc. Natl. Acad. Sci. USA 85:9138–9142.

Piper J, Rutovitz D, Sudar D, Kallioniemi A, Kallioniemi O P, Waldman F M, Gray J W, Pinkel D (1995) Computer image analysis of comparative genomic hybridization. Cytometry 19:10–26.

Pinkel D., Landegent J., Collins C., Fuscoe J., Segraves R., Lucas J. and Gray J. (1988) Fluorescent in situ hybridisation with human chromosome-specific libraries: Detection of trisomy 21 and translocation of chromosome 4. Proc. Natl. Acad. Sci. USA 85, 9138–9142.

Porath J., Carlsson J., Olsson I. and Belfrage G. (1975) Metal chelate affinity chromatography, a new approach to protein fractionation. Nature 258, 598–599.

Rouquier S, Trask B J, Taviaux S, van den Engh G, Diriong S, Lennon G G and Giorgi D (1995) Direct selection of cDNAs using whole chromosomes. Nucleic Acids Res. 23: 4415–4420.

Sachs R K, van den Engh G, Trask B, Yokota H, Hearst J E (1995) A random-walk/giant-loop model for interphase chromosomes. Proceedings of the National Academy of Sciences. USA. 92, 2710–2714.

Schena M, Shalon D, Davis R W, Brown P O (1995) Quantitative Monitoring of Gene Expression Patterns with a Complementary DNA Microarray. Science 25 270:467–470

Sealey P G., Whittaker P A. and Southern E M: (1985) Removal of repeated sequences from hybridisation probes. Nucleic Acids Res. 13: 1905–1922.

Shalon D., Smith S. J. and Brown P. O. (1996) A DNA Microarray system for Analysing complex DNA samples using two-color fluorescent probe hybridisation. Genome Research 6, 639–645.

Spector D L (1993) Macromolecular domains within the cell nucleus. Annu. Rev. Cell Biol. 9:265–315

Speicher M R, Ballard S G, Ward D C (1996) Karyotyping by combinatorial multifluor FISH, submitted Telenius H, Pelmear A H, Tunnacliffe A, Carter N P, Behmel A, Ferguson-Smith M A, Nordenskjöld M, Pfragner R, Ponder B A J (1992) Cytogenetic analysis by chromosome painting using DOP-PCR amplified flow-sorted chromosomes. Genes, Chromosomes Cancer 4, 257–263

Timberlake W. E. (1980) Dev. Biol. 78, 497–510).

Vooijs M, Yu L-C, Tkachuk D, Pinkel D, Johnson D and Gray J W (1993) Libraries for each human chromosome, constructed from sorter-emriched chromosomes by using linker-adapter PCR. Am J. Hum. Genet. 52: 586–597.

Welcher A. A., Torres A. R. and Ward D. C. (1986) Selective enrichment of specific DNA, cDNA and RNA sequences using biotinylated probes, avidin and copper-chelated agarose. Nucl. Acids Res. 14, 10027–10044

Weier H U G, Wang M, Mullikin J C, Zhu Y, Cheng J F, Greulich K M, Bensimon A, Gray J W (1995) Quantitative DNA fiber mapping. Human Molecular Genetics, 4,1903–1910

Wienberg J, Jauch A, Stanyon R, Cremer T (1990) Molecular cytotaxonomy of primates by chromosomal in situ suppression hybridization. Genomics 8: 341–350

Wienberg J, Stanyon R (1995) Chromosome painting in mammals as an approach to comarative genomics. Current Opinion in Genet. Develop. 5:792–797.

What is claimed is:

1. A method of purifying specific DNA molecules, comprising the steps of
   (a) mixing a set of DNA molecules as source DNA containing said specific DNA molecules as a subset, with a set of molecules as subtractor having substantially no affinity for the subset,
   (b) performing a binding reaction between source DNA and subtractor in solution,
   (c) separating the subtractor which is present unbound or bound to source DNA, by binding the subtractor to a matrix material containing compounds having an affinity to the subtractor, from the reaction mixture,
   (d) recovering said subset which is not bound to the subtractor, and
   (e) subjecting said recovered subset to PCR.

2. The method according to claim 1, wherein the subtractor is a set of DNA molecules and the binding reaction in step (b) is a hybridization.

3. The method according to claim 2, wherein the hybridization is performed by denaturing source DNA and subtractor mixed together in a buffer containing 0.075 M to 1.5 M NaCl, at 90 to 100° C. for 1 to 10 minutes and reannealing at 60 to 70° C. for 5 to 48 hours.

4. The method according to claim 2, wherein the hybridization is performed by denaturing source DNA and subtractor mixed together in a buffer containing 40 to 70% v/v formamide, 0.03 M to 0.75 M NaCl, at 60 to 80° C. for 1 to 10 minutes and reannealing at 30 to 50° C. for 5 to 48 hours.

5. The method according to claim 1, wherein the source DNA is a DNA probe used in FISH.

6. The method according to claim 1, wherein the source DNA comprises DNA of a defined function or a repeat-free chromosome-specific library.

7. The method according to claim 6, wherein the source DNA is selected from the group consisting of cDNA, CpG islands, scaffold-attached DNA and DNA of a defined replication time.

8. The method according to claim 1, wherein the subtractor is a set of labelled molecules.

9. The method according to claim 8, wherein the molecules are labelled with biotin, or digoxygenin.

10. The method according to claim 1, wherein the subtractor is Cot-1 DNA.

11. The method according to claim 1, wherein the subtractor comprises a repeat-free chromosome-specific library or DNA of a defined function.

12. The method according to claim 11, wherein the DNA of defined function is selected from the group consisting of cDNA, CpG islands, and scaffold-attached DNA.

13. The method according to claim 1, wherein the source DNA comprises repeat-free DNA from one species and the subtractor comprises repeat-free DNA from another species.

14. The method according to claim 1, wherein the source DNA comprises repeat-free DNA from one species or DNA sequences shared between two different species, and the subtractor is a repeat-free chromosome-specific library from another species.

15. The method according to claim 1, wherein the source DNA is a repeat-free chromosome-specific library from one species, and the subtractor comprises repeat-free DNA from another species or DNA sequences shared between two different species.

16. The method according to claim 1, wherein the source DNA comprises repeat-free DNA from one particular tissue and/or developmental stage, and the subtractor comprises repeat-free DNA of a defined function from another particular tissue and/or developmental stage of the same organism.

17. The method according to claim 1, wherein compounds contained in the matrix material used in step (c) are immobilized to the matrix material.

18. The method according to claim 17, wherein the matrix material contains streptavidin.

19. The method according to claim 17, wherein the matrix material is streptavidin-conjugated magnetic beads.

20. The method according to claim 1, wherein the source DNA contains thymidine analogs, the subtractor contains anti-thymidine analogues antibodies, and the matrix material contains compounds capable of binding to the anti-thymidine analogue antibodies.

21. The method according to claim 1, wherein the source DNA contains BrdU, the subtractor contains anti-BrdU antibodies, and the matrix material contains compounds capable of binding to the anti-BrdU antibodies.

22. The method according to claim 1, wherein prior to step (a), the source DNA are subjected to PCR.

23. The method according to claim 22, wherein the PCR is degenerate oligonucleotide-primed-PCR (DOP-PCR).

24. The method according to claim 23, wherein prior to step (a), the DOP-PCR-amplified source DNA is subjected to a further round of PCR with a primer whose 5'-portion comprises a sequence of nucleotides not present in the DOP primer used in claim 23, and whose 3'-portion consists of a number of the non-random nucleotides from the 5'-end of the DOP-primer used in claim 23.

25. The method according to claim 23, wherein the DOP-PCR primer has the sequence [SEQ ID NO.: 1]

5'-CCG ACT CGA GNN NNN NAT GTG G-3'
wherein N may be any nucleotide.

26. The method according to claim 24, wherein the second primer has the sequence [SEQ ID NOS. 2–3]

5'-CTA CTA CTA CTA CCG ACT CGA G-3', or
5'-TGA TCA CGC TAC CCG ACT CGA G-3'.

27. The method according to claim 1, wherein the PCR in step (e) is DOP-PCR.

28. The method according to claim 1, wherein steps (a) to (d) are repeated at least once using each recovered subset obtained in step (d) as source DNA in step (a).

29. A method of using the subset obtained according to the method of claim 1 as a probe for DNA-DNA hybridization, said method comprising a step of contacting said subset with a target DNA under conditions such that said subset forms a DNA-DNA hybrid with target DNA strands, if any, that have sequences complementary to sequences in DNA strands of said subset.

* * * * *

SEQUENCE LISTING

```
<160> NUMBER OF SEQ ID NOS:  3

<210> SEQ ID NO 1
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Description of Artificial Sequence:  DOP-PCR
      primer 6MW.
<221> NAME/KEY: misc_feature
<222> LOCATION: (10)..(16)
<223> OTHER INFORMATION: Nucleotides 10-16 are "n" wherein "n" = a or
      c or g or t/u or other

<400> SEQUENCE: 1
ccgactcgag nnnnnnatgt gg                                              22

<210> SEQ ID NO 2
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Description of Artificial Sequence:  DOP-PCR
      primer CTA4DOP.

<400> SEQUENCE: 2
ctactactac taccgactcg ag                                              22
```

```
<210> SEQ ID NO 3
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: Description of Artificial Sequence: further
      second DOP-PCR primer.

<400> SEQUENCE: 3
tgatcacgct acccgactcg ag                                          22
```